(12) United States Patent
Bonnet et al.

(10) Patent No.: US 11,865,309 B2
(45) Date of Patent: Jan. 9, 2024

(54) DRUG DELIVERY DEVICE WITH COATED END-PIECE

(71) Applicant: Becton Dickinson France, Le Pont de Claix (FR)

(72) Inventors: Stéphane Bonnet, Miribel Lanchatre (FR); Sylvain Hallynck, Sechilienne (FR)

(73) Assignee: Becton Dickinson France, Le Pont de Claix (FR)

( * ) Notice: Subject to any disclaimer, the term of this patent is extended or adjusted under 35 U.S.C. 154(b) by 873 days.

(21) Appl. No.: 15/515,024

(22) PCT Filed: Sep. 28, 2015

(86) PCT No.: PCT/EP2015/072276
§ 371 (c)(1),
(2) Date: Mar. 28, 2017

(87) PCT Pub. No.: WO2016/050699
PCT Pub. Date: Apr. 7, 2016

(65) Prior Publication Data
US 2017/0259003 A1 Sep. 14, 2017

(30) Foreign Application Priority Data
Sep. 29, 2014 (EP) ..................................... 14306523

(51) Int. Cl.
*A61M 5/31* (2006.01)
*A61M 39/10* (2006.01)
*A61M 5/14* (2006.01)

(52) U.S. Cl.
CPC ............ *A61M 5/3134* (2013.01); *A61M 5/14* (2013.01); *A61M 39/10* (2013.01);
(Continued)

(58) Field of Classification Search
CPC .. A61M 5/1413; A61M 5/3134; A61M 39/10; A61M 39/1011; A61M 2039/1077;
(Continued)

(56) References Cited

U.S. PATENT DOCUMENTS 4,326,569 A * 4/1982 Vaillancourt ....... A61M 39/045
141/383
4,589,871 A * 5/1986 Imbert .................. A61M 5/346
29/402.18
(Continued)

FOREIGN PATENT DOCUMENTS

EP 1466644 A2 10/2004
EP 1466644 B1 10/2006
(Continued)

*Primary Examiner* — Quynh-Nhu H. Vu
(74) *Attorney, Agent, or Firm* — The Webb Law Firm

(57) ABSTRACT

A drug delivery device includes a reservoir for containing a medical product, a distally projecting end-piece having an outer surface and a total length measured along a longitudinal axis of said end-piece, said end-piece defining an axial passageway for the transfer of said medical product contained in said reservoir, wherein a gripping surface is provided on a portion of said outer surface, said portion being located in a distal region of said end-piece, the length of said portion representing at most 40%, preferably less than 33%, of the total length of the end-piece. An assembly includes such a drug delivery device and an adaptor intended to be mounted onto the end-piece.

16 Claims, 3 Drawing Sheets

(52) U.S. Cl.
CPC . *A61M 39/1011* (2013.01); *A61M 2039/1077* (2013.01); *A61M 2205/0211* (2013.01); *A61M 2205/0238* (2013.01)

(58) Field of Classification Search
CPC ............ A61M 5/14; A61M 2205/0211; A61M 2205/0238; A61J 1/2048
See application file for complete search history.

(56) References Cited

U.S. PATENT DOCUMENTS

| | | | | |
|---|---|---|---|---|
| 5,624,402 | A * | 4/1997 | Imbert | A61M 5/3134 604/111 |
| 6,190,364 | B1 | 2/2001 | Imbert | |
| 6,196,998 | B1 * | 3/2001 | Jansen | A61M 5/3134 604/111 |
| 6,280,418 | B1 * | 8/2001 | Reinhard | A61M 5/28 604/181 |
| 6,969,375 | B2 * | 11/2005 | Thibault | A61M 5/344 604/241 |
| 7,350,764 | B2 * | 4/2008 | Raybuck | A61M 39/26 604/905 |
| 8,353,895 | B2 * | 1/2013 | Russo | A61M 25/0017 604/533 |
| 9,017,291 | B2 * | 4/2015 | Delabie | A61M 5/347 604/187 |
| 9,216,278 | B2 * | 12/2015 | Heinz | A61M 5/347 |
| 9,295,781 | B2 | 3/2016 | Siebers et al. | |
| 9,717,855 | B2 * | 8/2017 | Bosshardt | A61M 5/31 |
| 2001/0042850 | A1 * | 11/2001 | Cote, Sr. | A61M 39/02 251/149.1 |
| 2004/0067161 | A1 * | 4/2004 | Axelsson | A61M 1/288 604/534 |
| 2010/0280462 | A1 | 11/2010 | Kommireddy et al. | |
| 2011/0095528 | A1 | 4/2011 | Forberg | |
| 2012/0116355 | A1 * | 5/2012 | Heinz | A61M 39/1011 604/535 |
| 2012/0179108 | A1 * | 7/2012 | Delabie | A61M 5/347 604/187 |
| 2013/0158485 | A1 * | 6/2013 | Siebers | A61M 5/346 604/187 |
| 2014/0012204 | A1 * | 1/2014 | Bosshardt | A61M 39/1011 604/187 |
| 2014/0346417 | A1 | 11/2014 | Nurnberger | |
| 2022/0088311 | A1 * | 3/2022 | Gruber | A61M 5/31 |

FOREIGN PATENT DOCUMENTS

| | | |
|---|---|---|
| EP | 2138202 A1 | 12/2009 |
| EP | 2138202 B1 | 12/2009 |
| EP | 2606928 A2 | 6/2013 |
| EP | 2606928 P | 6/2013 |
| JP | 663049 U | 9/1994 |
| JP | 8215307 A | 8/1996 |
| JP | 2005143832 A | 6/2005 |
| JP | 2012530586 A | 12/2012 |
| WO | 2013083439 A1 | 6/2013 |

* cited by examiner

DRUG DELIVERY DEVICE WITH COATED END-PIECE

CROSS-REFERENCE TO RELATED APPLICATIONS

This application is the United States national phase of International Application No. PCT/EP2015/072276 filed Sep. 28, 2015, and claims priority to European Patent Application No. 14306523.3 filed Sep. 29, 2014, the disclosures of which are hereby incorporated in their entirety by reference.

BACKGROUND OF THE INVENTION

Field of the Invention

The present disclosure relates to a drug delivery device having an end-piece provided with a gripping surface.

The present disclosure relates to a drug delivery device intended to be used with an adaptor. The drug delivery device is provided with an end-piece around which the adaptor is engageable so as to enable the safe connection of a connector on said end-piece.

DESCRIPTION OF RELATED ART

Drug delivery devices usually include a hollow body forming a reservoir for containing a medical product. In addition, the distal end of the body forming the reservoir usually includes an end-piece in which an axial passageway is arranged and through which said medical product is ejected from the reservoir.

In this application, the distal end of a component or of a device must be understood as meaning the end furthest from the hand of the user and the proximal end must be understood as meaning the end closest to the hand of the user. Similarly, in this application, the distal direction must be understood as the direction of injection or transfer of the product (i.e. from the reservoir to an Intra Venous line for example) and the proximal direction is the opposite direction.

The handling of products, such as liquid medicine, in particular for a parenteral administration to a patient which is carried out via a perfusion device, as often in hospitals or in emergency situations, implies, in general, the use of connectors, such as IV (Intra Venous) connectors which join together the drug delivery device, containing the product to be delivered, and the vein of the patient, usually via an IV line. Of course, the drug delivery device, in particular its end-piece, and the connector must be assembled together correctly and securely.

Indeed, it is important that the connection between the drug delivery device and the connector is strong enough to prevent accidental disengagement, either during connection of the connector onto the drug delivery device, or caused by the fluid pressures within the drug delivery device and connector. If the end-piece of the drug delivery device is disengaged from the connector, the medical product such as drug, blood or any other fluid, will be lost. In addition, in such cases, there would be a potential contamination of the medical product.

Actually, there are different connection systems for connecting a connector to the end-piece of a drug delivery device, when the distal portion of said end-piece has the global shape of a distally tapered cone, also called a male luer, as is usually the case.

In such cases, the male luer of the end-piece forming the male part of the connection system, the connector usually includes a corresponding conical bore forming the female part of the connection system, also called a female luer, and intended to be fitted on the male luer in order to complete the connection.

In some cases, no additional element is provided on the connector, and the female luer is directly fitted on the male luer of the end-piece of the drug delivery device by simple force fitting: the connector is then called a luer slip connector and the connection is called a luer slip connection.

Alternatively, the connection system may also include an adaptor, said adaptor being plugged to the end-piece of the drug delivery device via a collar, and including a tubular wall at least partially surrounding the male luer of the end-piece. The tubular wall is provided with an inner thread intended to cooperate with a corresponding outer thread located on an outer wall of the connector provided with the female luer. In such a case, at the time of forming the connection, the female luer is fitted onto the male luer by means of threading the connector in the adaptor: the safe connection of the male luer and female luer is therefore improved. Such an adaptor is called a luer lock adaptor, the connector is called a luer lock connector and the connection thus achieved is called a luer lock connection. Instead, the thread of the connector may be replaced by cooperating wings.

In the field of connection systems for medical devices, the reliability of the connection is a very important factor. Indeed, much of the torque applied during the connection of a connector to the end-piece of a drug delivery device is transmitted to the adaptor. The end-piece being usually made of glass or plastic materials, its surface is rather smooth, so that the adaptor mounted on said end-piece may be caused to rotate under the effect of the transmitted torque and the connection may not be correctly completed.

In some applications, in order to enhance the reliability of a luer slip connection, it has been proposed to apply a coating on the outer surface of the male luer so as to increase the roughness of said surface and provide more resistance by friction between the female luer and the male luer. In general, with such a coating, the force required to remove the connector from the end-piece, on which it is removably connected by a frictional interference fit, is greater than the force required to remove the connector from an identically sized end-piece without any coating applied on its outer surface.

Nevertheless, it has been observed that when such coated male luers are used in association with a luer lock adaptor, the efficiency of the connection system decreases dramatically. Indeed, the luer lock adaptor loses its capability of resisting disconnection by friction. In the end, the connection of the connector on the adaptor and on the male luer is not reliable.

It would therefore be desirable to provide a drug delivery device with an end-piece, such as a male luer, capable of enhancing the reliability of the connection between such end-piece and a connector, when the drug delivery device is used in combination with a luer lock adaptor.

SUMMARY OF THE INVENTION

It has been found that by creating a gripping surface at a specific location of the outer surface of the end-piece of a drug delivery device, so that the roughness of the outer surface of the end-piece is increased on a specific portion of said outer surface, it was possible not only to avoid the dramatic loss of efficiency of the connection, but also to extend the reliability of the connection, compared to a system where the outer surface of the end-piece is not modified.

A first aspect of the disclosure is a drug delivery device including:
- a reservoir for containing a medical product,
- a distally projecting end-piece having an outer surface and a total length $L_T$ measured along a longitudinal axis A of said end-piece, said end-piece defining an axial passageway for the transfer of said medical product contained in said reservoir,
- wherein a gripping surface is provided on a portion of said outer surface, said portion being located in a distal region of said end-piece, the length $L_C$ of said portion representing at most 40%, preferably less than 33%, of the total length $L_T$ of the end-piece.

The drug delivery device of the invention is intended to be used in combination with an adaptor including a collar intended to be mounted onto the end-piece of said drug delivery device.

The end-piece of the drug delivery device of the invention defines a passageway, for example a channel, for the transfer of the medical product contained in the reservoir towards another medical device or a needle in a view of proceeding to an injection for example. The end-piece may be made of glass or of plastic material. As such, the outer surface of the end-piece of the drug delivery device of the invention is rather globally even and smooth.

"Gripping surface" means according to the present application a surface having an increased roughness with respect to outer surfaces of end-pieces conventionally used in drug delivery devices, such as glass or plastic materials end-pieces, the outer surfaces of which are smooth and even. For example, the structure of the gripping surface of the device of the disclosure allows increasing the force required for removing a connector removably connected to the end-piece by frictional interference fit, compared to the force that would be required for the same operation, but on a conventional end-piece, free of any gripping surface. In particular the gripping surface of the device of the invention may show roughness or reliefs, such as peaks and downs, with height variations.

The end-piece of the drug delivery device of the disclosure has a longitudinal axis and has therefore rather an elongated shape aligned on said longitudinal axis. As such, it can define a proximal region and a distal region of said end-piece. For example, if the end-piece has a total length $L_T$ measured along longitudinal axis A, the proximal region may correspond to half the length $L_T$ in the proximal direction, while the distal region of the end-piece encompasses the other half of the length $L_T$ of the end-piece in the distal direction.

In the present application, the total length $L_T$ of the end-piece and the length $L_C$ of the portion including the gripping surface are measured along the direction of the longitudinal axis A.

In the drug delivery device of the disclosure, the gripping surface is located in the distal region of the outer surface of the end-piece and the length $L_C$ of the portion of the outer surface on which said gripping surface extends represents at most 40%, preferably less than 33%, of the total length $L_T$ of the end-piece. The portion on which the gripping surface extends is therefore limited and it is located far away from the proximal end of the end-piece and outside from the proximal region of the end-piece. Because the portion of the outer surface on which said gripping surface extends represents at most 40%, preferably less than 33%, of the total length $L_T$ of the end-piece, such gripping surface is not present in excess on the outer surface of the end-piece and is neither present in areas of the end-piece where it is not wished. Moreover, since the gripping surface is provided on a portion of the outer surface of the end-piece which is located in the distal region of the outer surface of the end-piece, said gripping does not extend outside of the outer surface of the end-piece.

When the drug delivery device of the disclosure is used in combination with an adaptor as described above, namely an adaptor including a collar intended to be mounted onto the end-piece of said drug delivery device, the connection thus achieved is particularly reliable. In particular, the collar of the adaptor maintains its capability to be fixed to the proximal region of the end-piece via friction forces. As a consequence, when the connector is threaded onto the adaptor, the adaptor remains in place onto the end-piece, and the threading may be completed in an efficient manner. Indeed, the presence of the gripping surface in a specific proportion of the length $L_T$ of the end-piece and at a specific place on the outer surface of the end-piece increases the capability of the adaptor to resist to the torque applied by the user when threading the connector into the adaptor. As a result, the connection of a connector to the end-piece of the drug delivery device of the disclosure via the adaptor is reliable. Moreover, the gripping surface provides additional friction forces between the inner surface of the female luer of the connector and the outer surface of the end-piece, thereby leading to an increased reliability of the connection, compared to a system where the outer surface of the end-piece is not modified.

In embodiments, a distal edge of said portion is located at least at 0.5 mm from a distal end of the end-piece. In other embodiments, said distal edge is located at around 1 mm from the distal end of the end-piece. For clarification, since the portion on which is provided the gripping surface is located in the distal region of the outer surface of the end-piece as seen above, the distal edge of said portion is located on the outer surface of the end-piece and not outside of the outer surface of the end-piece. For example, the distal edge of said portion is proximally spaced with respect to the distal end of the end-piece. As will appear from the description below, such embodiments increase the efficiency of the adaptor by limiting the risks that said adaptor contacts the gripping surface when the adaptor is mounted onto the end-piece.

In embodiments, the end-piece has a frustoconical shape, the outer diameter of the distal end of said end-piece being less than the outer diameter of the proximal end of said end-piece. For example, the end-piece may be a male luer in conformity with Standard ISO594 or ISO11040. In such cases, the end-piece is a frustoconical tip having a 6% taper. For example, in such cases, the total length LT of the end-piece may vary from 7.5 mm to 7.8 mm.

In embodiments, the total length $L_T$ of said end-piece varying from 7.5 mm to 7.8 mm, the length $L_C$ of said portion varies from 2.00 mm to 2.70 mm, preferably is around 2.35 mm.

As mentioned before, the structure and/or nature of the gripping surface allows increasing the force required for removing a connector removably connected to an end-piece by frictional interference fit, compared to the force that would be required for the same operation, but on an end-piece free of any coating.

The gripping surface may result from a modification of the surface of the material forming the end-piece, such as glass or plastic materials. For example, such modification may be provided by a technique for modifying external surfaces of materials in general. In embodiments, the modification is provided by a technique selected from abrasion technique, forming treatment, plasma treatment, laser treatment and combinations thereof, applied on said portion. For example, the gripping surface may result from an abrasion of the outer surface of the material forming the end-piece on said portion. Alternatively or in combination, the gripping surface may result from a plasma treatment of the outer surface of the material forming the end-piece on said portion. Alternatively or in combination, the gripping surface may result from a laser or forming treatment of the outer surface of the material forming the end-piece on said portion.

Alternatively or in combination, the gripping surface may be part of a supplementary piece provided on said portion. For example, the gripping surface may be formed by the outer surface of a material showing naturally the gripping features mentioned above in the definition of the gripping surface. A material showing naturally gripping features suitable for the present invention may be an elastomeric material. In embodiments, the gripping surface is the outer surface of an elastomeric sleeve attached or molded to said portion of said end-piece.

Alternatively or in combination, the gripping surface is provided by application of a coating on said portion. In embodiments, the coating is a ceramic coating including borosilicate-zinc based frits. Such a coating confers additional roughness to the outer surface of the end-piece on said portion. Any coating composition which, when cured or dried, increases the roughness of the outer surface of the end-piece so that the force required to remove the connector from the end-piece, on which it is removably connected by a frictional interference fit, is greater than the force required to remove the connector from an identically sized end-piece free of any gripping surface, may be contemplated in the present disclosure.

The gripping surface may be uniform in nature and structure or on the contrary may be a combination of a modified surface, an added part having natural gripping features and a coating, as mentioned above. The gripping surface may show a specific pattern. The pattern may include a band or a shape of waves, or any design that allows increasing the gripping properties of the outer surface of the end-piece as described above.

In embodiments, the end-piece is made of glass and the gripping surface is provided by application of a ceramic coating. The presence of the ceramic coating on an end-piece made of glass is very efficient for increasing the friction forces between the end-piece and the adaptor.

In embodiments, the end-piece further includes an annular groove located in a proximal region on its outer surface. As will appear from the description below, such a groove is intended to cooperate with a rim located on the collar of an adaptor intended to be engaged on the end-piece, in particular for providing a reliable connection between the end-piece and the adaptor.

Another aspect of the disclosure is an assembly including a drug delivery device as described above and an adaptor including a collar intended to be mounted on said end-piece.

In embodiments, the collar is provided with an inner rim intended to be engaged into the annular groove, when the adaptor is mounted on the end-piece. In particular, the adaptor is intended to be fixed onto the end-piece by frictional interference fit between the inner rim and the annular groove.

BRIEF DESCRIPTION OF THE DRAWINGS

The drug delivery device and assembly of the disclosure will now be further described in reference to the following description and attached drawings in which.

DETAILED DESCRIPTION OF THE INVENTION

Figure 1:
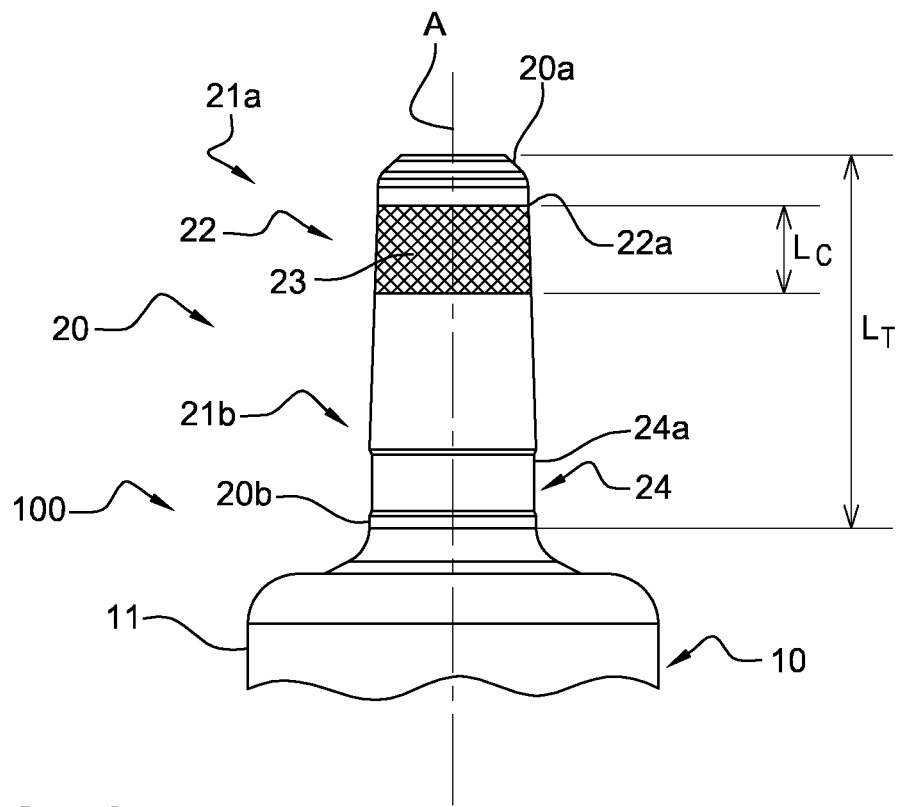
FIG. 1 is a partial side view of an embodiment of the drug delivery device of the disclosure.

With reference to FIG. 1 is shown partially a drug delivery device 100 of the disclosure including a reservoir 10 having a distally projecting end-piece 20 aligned on a longitudinal axis A.

The reservoir 10 is intended to contain a medical product to be delivered to a patient. The reservoir 10 may be formed of any material suitable for storing a product such as a medicine or drug. It may be made of glass or plastic materials. On the example shown, the reservoir 10 has the global shape of a syringe body and includes a tubular barrel 11. The tubular barrel 11 is open at its proximal end (not shown) for example for receiving a stopper. The end-piece 20 includes an axial passage way (not visible on the figure) for the transfer of the product contained in the reservoir. For example, the product may be transferred from the reservoir to another medical device, such as a connector to an IV line, etc.

On FIG. 1, the end-piece 20 has a frustoconical shape, the outer diameter of its distal end 20*a* being less than the outer diameter of its proximal end 20*b*. The end-piece 20 has a distal region 21*a* and a proximal region 21*b*.

For example, the end-piece is a male luer according to a standard, for example ISO594 or ISO11040 and the slope of the cone is 6%. In such a case, the total length $L_T$ of the end-piece may vary from 7.5 mm to 7.8 mm.

The end-piece may be made of glass or of plastic material.

In the proximal region of its outer surface, the end-piece 20 includes an annular groove 24, provided with an axial surface 24*a*, the function of which will be explained later.

In embodiments not shown, the outer surface of the end-piece is free of any annular groove or relief.

On a portion 22 of the outer surface of its distal region 21*a*, the end-piece 20 is provided with a gripping surface, under the form of a coating 23 on the example shown. The coating 23 is capable of increasing the roughness of the outer surface of the end-piece 20.

For example, the coating is a ceramic coating including borosilicate-zinc based fits. Such a coating confers additional roughness to the outer surface of the end-piece. Any coating composition which, when cured or dried, increases the roughness of the surface of the end-piece so that the force required to remove the connector from the end-piece, on which it is removably connected by a frictional interference fit, is greater than the force required to remove the connector from an identically sized end-piece without the coating, may be contemplated in the present disclosure. Examples of coating compositions are mixtures of borosilicate and zinc based frits.

The coating may be obtained by deposition of the ceramic solution onto the outer surface of the end-piece by means of a wheel soaking in suspension in the solution. A pre-defined layer of ceramic coating in the range of no more than 150 μm width, for example ranging from 10 to 150 μm width, is deposited onto the outer surface of the end-piece. Then, the drug delivery device is put in an annealing oven. The ceramic coating is dried cured.

The coating may be uniform in nature. It may be applied onto the outer surface of the end-piece under the form of a specific pattern, said pattern being present on the wheel. The pattern may include any design that allows increasing the roughness of the outer surface of the end-piece as described above.

In other embodiments not shown, the gripping surface, formed of the coating 23 in the example of the figures, may result from a modification of the surface of the material forming the end-piece, such as glass or plastic materials. For example, the modification may be provided by a technique selected from abrasion technique, plasma treatment, laser treatment and combinations thereof, applied on said portion. Alternatively or in combination, the gripping surface may be part of a supplementary piece provided on said portion. For example, the gripping surface may be the outer surface of an elastomeric sleeve attached, molded or co-molded, to said portion of said end-piece, depending on the nature, i.e. glass or plastic, of said portion.

With reference to FIG. 1, the coating 23 is located in the distal region 21a of the outer surface of the end-piece 20. In addition, the length $L_C$ of the portion 22 measured along the longitudinal axis A represents at most 40%, preferably less than 33%, of the total length $L_T$ of the end-piece also measured along longitudinal axis A.

The distal edge 22a of the portion 22 on which the coating 23 extends may be located at around 0.5 mm, preferably at 1 mm, from the distal end 20a of the end-piece 20. As appears on FIG. 1, the distal edge 22a is proximally spaced with respect to the distal end 20a of the end-piece 20.

For example, the total length $L_T$ of the end-piece 20, measured from its proximal end 20b to its distal end 20a, along the longitudinal axis A, may vary from 7.5 to 7.8 mm. In such a case, the length $L_C$ of the portion 22 on which the coating extends may for example vary from 2.00 to 2.70 mm. For example, this length $L_C$ may be 2.35 mm. In such a case, the portion on which the coating 23 extends represents around 30-32% of the total length $L_T$.

Figure 5:
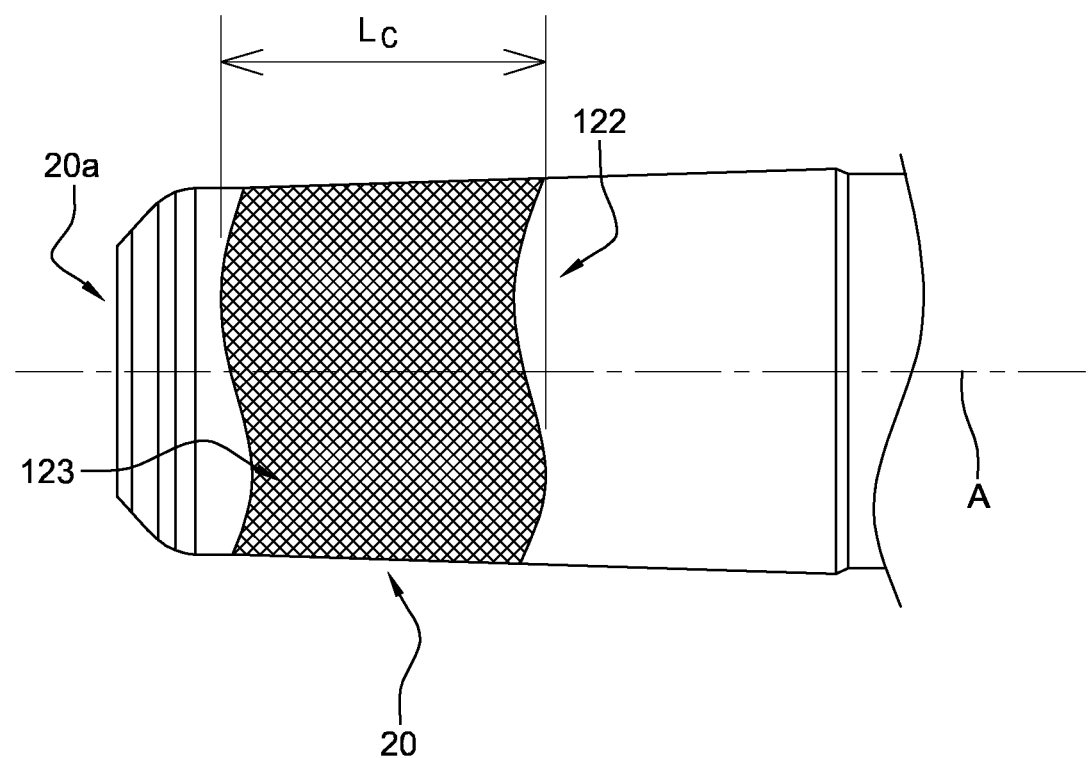
FIG. 5 is a partial side view of another embodiment of an end-piece of the drug delivery device of the disclosure.

On FIG. 1, the coating has the shape of an annular band and said coating 23 extends on the totality of the portion 22, as the surface of the portion 22 is common with the surface of the coating 23. With reference to FIG. 5, is shown another embodiment of an end-piece of a drug delivery device of the disclosure. The references designating the same elements as in FIG. 1 have been maintained. On the embodiment of FIG. 5, the coating 123 has the shape of a band forming waves. The surface of the portion 122 on which the coating 123 extends is therefore greater than the surface of the coating. Anyway, the length $L_C$ of the portion 122 still represents at most 40% of the total length of the end-piece.

Figure 2:
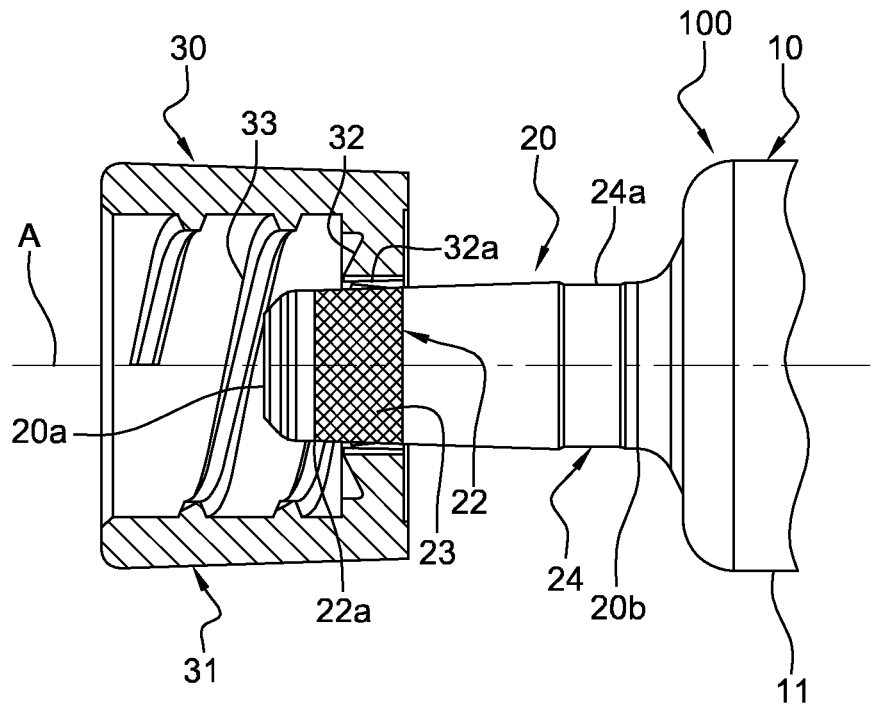
FIG. 2 is a partial side view of an adaptor being mounted onto the end-piece of the drug delivery device of FIG. 1.

With reference to FIG. 2, is shown the mounting of an adaptor 30 on the end-piece 20. The adaptor 30 includes a collar 31 provided at its proximal end with an inner rim 32 having an axial surface 32a. As will be clear from the description below, the adaptor 30 is intended to be fixed onto the end-piece 20 by frictional interference fit between the inner rim 32 and the annular groove 24 of the end-piece 20.

The inner surface of the collar 31 is provided with an inner thread 33, the function of which will be explained later. The mounting of the adaptor 30 onto the end-piece 20 is facilitated by the appropriate location of the coating 23 on the end-piece 20 and also by the small length $L_C$ of the coated part of the end-piece, said length $L_C$ representing namely less than 40%, preferably less than 33%, of the total length $L_T$ of the end-piece. In particular, as shown on this FIG. 2, it is possible to slide the adaptor 30 over the end-piece 20 while avoiding that the inner rim 32 of the adaptor contacts the coating 23. Neither the coating 23 nor the axial surface 32a of the inner, rim 32 of the adaptor 30 are damaged by mutual contact, since such mutual contact does not take place.

In particular, because of the location of the distal edge 22a of the portion 22 on which the coating 23 extends, at least 0.5 mm, preferably 1 mm, away from the distal end 20a of the end-piece 20 in the proximal direction, the risk that the adaptor 30 contacts the coating 23 when said adaptor 30 is approached towards the end-piece 20 is very limited. In addition, thanks to this configuration, no particles are generated and contamination is therefore avoided.

For example, the inner diameter of the inner rim 32 is greater than the greatest outer diameter of the portion 22 so that contact between the inner rim 32 and the outer surface of the portion 22 is avoided when the adaptor is being mounted on the end-piece, and potential damage likely to occur from such a contact is therefore prevented. In particular, emission of particles which could result from the contact between the inner rim 32 and the outer surface of the portion 22 at the time the adaptor is being mounted on the end-piece is avoided. The quality of the drug delivery device therefore remains high.

Figure 3:
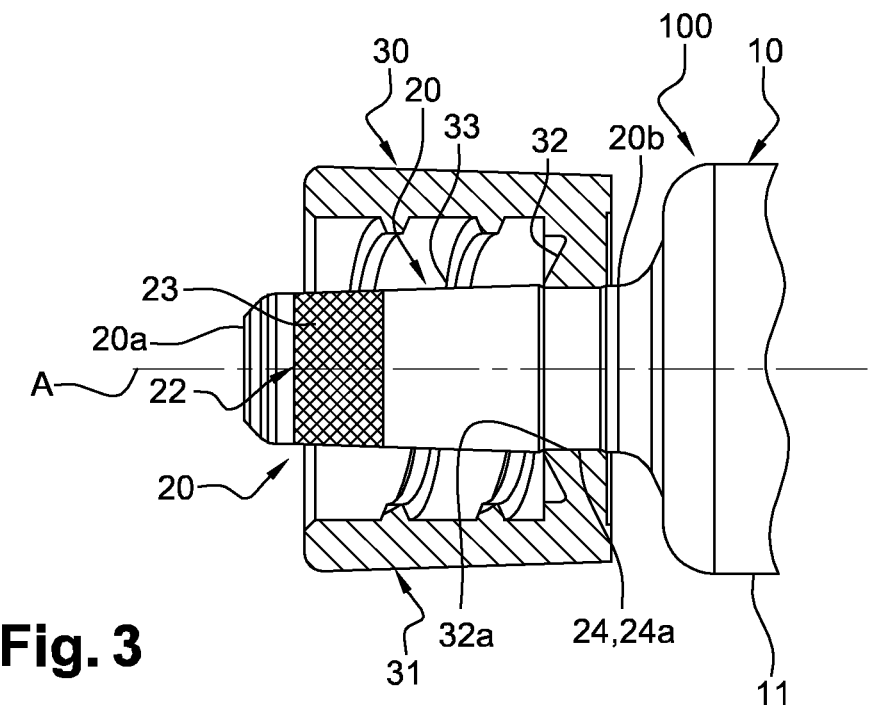
FIG. 3 is a partial side view of the assembly of FIG. 2 once the adaptor is mounted onto the end-piece of the drug delivery device.

With reference to FIG. 3, the adaptor 30 has been fully mounted onto the end-piece 20. The inner rim 32 of the adaptor 30 is now engaged into the annular groove 24 of the end-piece 20, with its axial surface 32a in contact with the axial surface 24a of said groove 24. The adaptor 30 is therefore fixed onto the end-piece 20 by friction forces present between the axial surface 32a of the inner rim 32 and the axial surface 24a of the annular groove 24. In particular, because the axial surface 32a of the inner rim 32 has not been in contact with the coating 23 during the mounting of the adaptor 30 onto the end-piece 20, the adaptor 30 does not lose its capability of remaining in friction fit with the end-piece. The fixation of the adaptor 30 on the end-piece 20 is therefore reliable. A connector may then be threaded into the adaptor safely.

Figure 4:
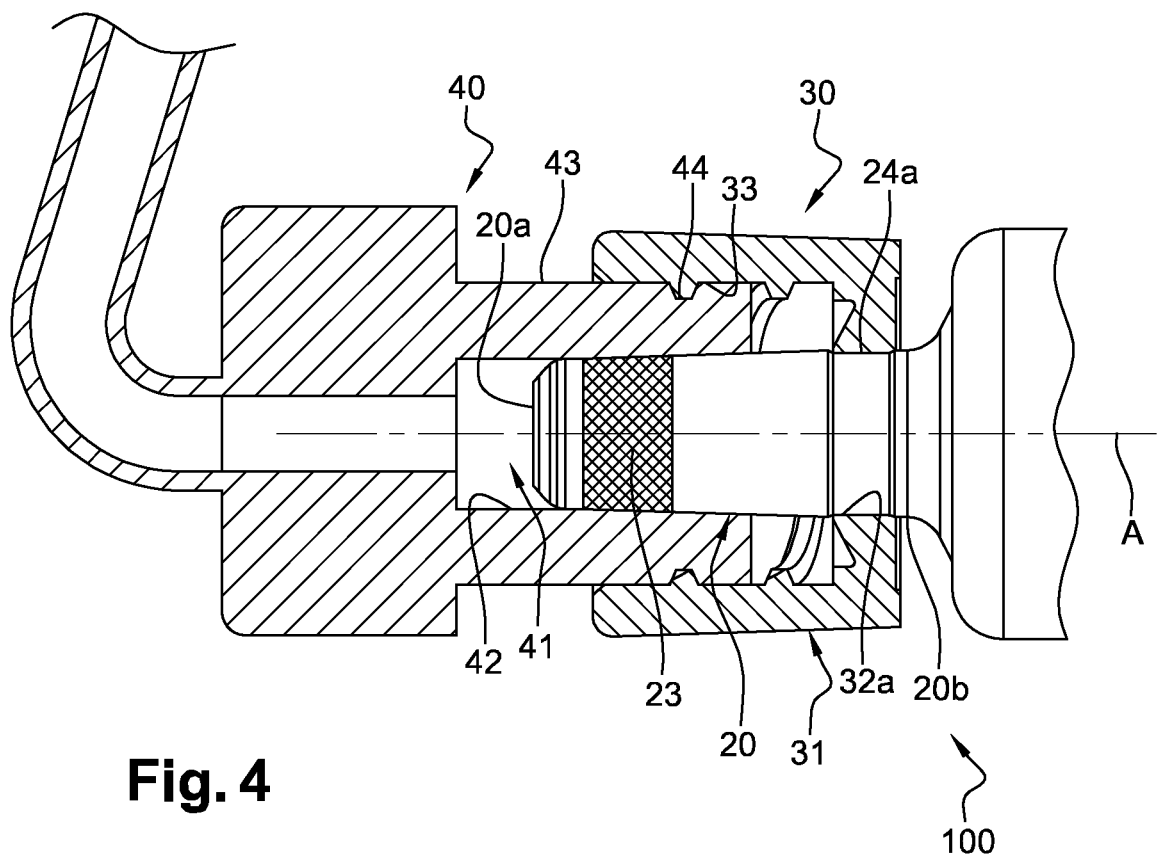
FIG. 4 is a partial side view of a connector connected to the assembly of FIG. 3.

With reference to FIG. 4, is shown a connector 40, under the form of the proximal end of an Intra venous line, which has been threaded into the adaptor 30.

The connector 40 includes a female luer 41 having an inner surface 42. On its outer surface 43, the female luer 41 is provided with an outer thread 44 capable of cooperating with the inner thread 33 of the adaptor 30.

Because the adaptor 30 is well fixed to the end-piece 20 thanks to the friction forces between the end-piece 20 and the adaptor 30 as described above, the threading of the connector 40 into the adaptor 30 is facilitated. Besides, the coating 23 is in tight contact with the inner surface 42 of the female luer of the connector 40. This tight contact between the coating 23 of the end-piece 20 and the inner surface 42 of the female luer 41 provides additional friction forces between the adaptor 30 and the end-piece 20, thereby enhancing the reliability of the connection there between. In particular, when the connector 40 is threaded into the adaptor 30, the presence of the coating 23 increases the resistance of the adaptor 30 to the torque provided by the user in view of threading the connector 40 into the adaptor 30. As a consequence, the adaptor 30 remains immobile and does not rotate with respect to the end-piece 20, contrarily to what may happen with the end-pieces of the prior art free of any gripping surface. The threading of the connector 40 into the adaptor 30 is therefore not only facilitated but also more reliable and secure.

A test measuring the pull out force (POF) of a drug delivery device of the invention and of a drug delivery device of the prior art has been completed. The drug delivery device of the invention is provided with the end-piece of FIG. 1, in which the gripping surface is a ceramic coating including borosilicate-zinc based frits. The end-piece is a frustoconical tip having a 6% taper, made of glass. An adaptor such as the adaptor 30 of FIG. 2 is mounted on the frustoconical tip.

The comparative drug delivery device is provided with a standard frustoconical tip having a 6% taper, made of glass, free of any gripping surface. An adaptor such as the adaptor 30 of FIG. 2 is mounted on the frustoconical tip.

The Pull Out Force test includes connecting a connector by threading the connector into the adaptor mounted on the frustoconical tip by applying a torque of 12 Ncm by automatic torque-meter combined with an axial force of 20N and then measuring the force to remove the adaptor from the frustoconical tip by pulling the connector while the drug delivery device is fixed.

The median value of the force in Newton necessary for achieving the aim of the Pull Out Force test with the drug delivery device of the invention was 135 N, whereas that required for the comparative drug delivery device was 58 N. These results show that the reliability of the connection between the end-piece and the connector is increased in the drug delivery device compared to a drug delivery device of the prior art.

A test measuring the torque for disconnecting a connector from a drug delivery device of the disclosure and from a drug delivery device of the prior art has been completed. The drug delivery device of the invention and the comparative drug delivery device are identical to those described above for the Pull Out Force test.

The Torque test consists in first connecting a connector by threading the connector into the adaptor mounted on the frustoconical tip by applying a torque of 12 Ncm by automatic torque-meter combined with an axial force of 20 N. Then, an unscrewing torque of 2 Ncm is applied on the connector during 10 seconds, and the potential disconnection is checked. The unscrewing torque is then increased until disconnection of the connector.

The median value of the torque necessary for achieving the aim of the test with the drug delivery device of the invention was 23 Ncm while that required for the comparative drug delivery device was 14 Ncm. These results show that the reliability of the connection between the end-piece and the connector is increased in the drug delivery device compared to a drug delivery device of the prior art.

The drug delivery device of the disclosure allows increasing the reliability of a connection between the end-piece of such a drug delivery device and a connector, especially in the case when such drug delivery device is intended to be used in combination with an adaptor such as a luer lock adaptor.

While various examples of the drug delivery device were provided in the foregoing description, those skilled in the art may make modifications and alterations to these examples without departing from the scope and spirit of the disclosure. For example, it is to be understood that this disclosure contemplates that, to the extent possible, one or more features of any example can be combined with one or more features of any other example. Accordingly, the foregoing description is intended to be illustrative rather than restrictive. The disclosure described hereinabove is defined by the appended claims and all changes to the disclosure that fall within the meaning and the range of equivalency of the claims are to be embraced within their scope.

The invention claimed is:

1. A drug delivery device comprising:
a reservoir for containing a medical product, and
a distally projecting frustoconical end-piece having an outer surface and a total length measured along a longitudinal axis of said end-piece, said end-piece defining an axial passageway for a transfer of said medical product contained in said reservoir, said end-piece having a proximal region configured to be fixed to an adaptor,
wherein a gripping surface is provided on a portion of said outer surface, said portion being located in a distal half of said end-piece and outside a proximal half forming the proximal region of the end-piece, a length of said portion representing at most 40% of the total length of the end-piece,
wherein the end-piece comprises an annular groove located in the proximal region on the outer surface of the end-piece, and further wherein the proximal region and the annular groove do not include the gripping surface,
wherein the annular groove has a diameter less than at least a portion of the proximal region, and wherein the annular groove engages entirely with an inner surface of a collar of the adapter, and
wherein the portion of the outer surface having the gripping surface is spaced apart from the inner surface of the collar of the adapter such that the adapter does not contact the gripping surface when being slid over the end-piece.

2. The drug delivery device according to claim 1, wherein a distal edge of said portion of said outer surface is located at least at 0.5 mm from a distal end of the end-piece.

3. The drug delivery device according to claim 1, wherein an outer diameter of a distal end of said end-piece is less than an outer diameter of a proximal end of said end-piece.

4. The drug delivery device according to claim 1, wherein the total length of said end-piece varies from 7.5 mm to 7.8 mm, the length of said portion of said outer surface varies from 2.00 mm to 2.70 mm.

5. The drug delivery device according to claim 4, wherein said length of said portion of said outer surface is around 2.35 mm.

6. The drug delivery device according to claim 1, wherein the gripping surface results from a modification of a surface of a material forming the end-piece.

7. The drug delivery device according to claim 6, wherein the modification is provided by a technique selected from abrasion technique, forming treatment, plasma treatment, laser treatment and combinations thereof, applied on said portion of said outer surface.

8. The drug delivery device according to claim 1, wherein the gripping surface is part of a supplementary piece provided on said portion of said outer surface.

9. The drug delivery device according to claim 8, wherein the gripping surface is an outer surface of an elastomeric sleeve attached or molded to said portion of said outer surface of said end-piece.

10. The drug delivery device according to claim 1, wherein the gripping surface is provided by application of a coating on said portion of said outer surface.

11. The drug delivery device according to claim 10, wherein the coating is a ceramic coating comprising borosilicate-zinc based frits.

12. The drug delivery device according to claim 10, wherein the end-piece is made of glass.

13. An assembly comprising a drug delivery device according to claim 1, wherein the collar is mountable on the end-piece.

14. The assembly according to claim 13, wherein the collar is provided with an inner rim engageable in the annular groove, when the adaptor is mounted on the end-piece.

15. The drug delivery device according to claim 1, wherein the length of said portion of said outer surface represents less than 33% of the total length of the end-piece.

16. The drug delivery device according to claim 1, wherein a distal edge of said portion of said outer surface is located at least 1 mm from a distal end of the end-piece.

* * * * *

UNITED STATES PATENT AND TRADEMARK OFFICE
CERTIFICATE OF CORRECTION

PATENT NO. : 11,865,309 B2
APPLICATION NO. : 15/515024
DATED : January 9, 2024
INVENTOR(S) : Stéphane Bonnet et al.

It is certified that error appears in the above-identified patent and that said Letters Patent is hereby corrected as shown below:

In the Claims

Column 11, Line 18, Claim 14, delete "groove," and insert -- groove located in the proximal region on the outer surface of the end-piece --

Signed and Sealed this
Fifth Day of March, 2024

Katherine Kelly Vidal
*Director of the United States Patent and Trademark Office*